United States Patent [19]

Silverman et al.

[11] Patent Number: 5,773,665
[45] Date of Patent: Jun. 30, 1998

[54] HYDROFORMYLATION PROCESS WITH SEPARATION AND RECYCLE OF ACTIVE RHODIUM CATALYST

[75] Inventors: Gary Stephen Silverman, Chaddsford; Paul Mercando, Pennsburg, both of Pa.

[73] Assignee: ELF Atochem North America, Inc., Philadelphia, Pa.

[21] Appl. No.: 683,593

[22] Filed: Jul. 15, 1996

Related U.S. Application Data

[60] Provisional application No. 60/001,222 Jul. 18, 1995.

[63] Continuation-in-part of Ser. No. 673,983, Jul. 1, 1996.

[51] Int. Cl.$^6$ .................................................. C07C 45/50
[52] U.S. Cl. ............................................ 568/451; 568/454
[58] Field of Search .................................... 568/451, 454

[56] References Cited

U.S. PATENT DOCUMENTS

| | | | |
|---|---|---|---|
| 2,945,743 | 7/1960 | Zimmerley et al. . | |
| 3,547,964 | 12/1970 | Olivier | 260/429 |
| 3,560,539 | 2/1971 | Booth | 260/429 |
| 3,567,368 | 3/1971 | Nekvasil et al. . | |
| 3,755,393 | 8/1973 | Kniese et al. | 260/429 |
| 3,998,622 | 12/1976 | Balmat . | |
| 4,113,754 | 9/1978 | Kummer et al. | 260/429 |
| 4,135,911 | 1/1979 | Balmat . | |
| 4,292,196 | 9/1981 | Homeier et al. | 252/412 |
| 4,363,765 | 12/1982 | Fiato et al. | 260/429 |
| 4,388,279 | 6/1983 | Quick | 423/22 |
| 4,396,551 | 8/1983 | Tsunoda et al. . | |
| 4,413,118 | 11/1983 | Roberts et al. . | |
| 4,935,550 | 6/1990 | Miller et al. | 568/454 |
| 4,944,927 | 7/1990 | Gulliver | 423/22 |
| 4,950,629 | 8/1990 | Bodurow | 502/24 |
| 5,114,473 | 5/1992 | Abatjoglou et al. | 75/722 |
| 5,208,194 | 5/1993 | Pitchai et al. | 502/12 |

*Primary Examiner*—Gary Geist
*Assistant Examiner*—Sreeni Padmanabhan
*Attorney, Agent, or Firm*—Stanley A. Marcus; Nicholas J. DeBenedictis

[57] ABSTRACT

Active Rhodium catalyst and impurities are separated from a hydroformylation process stream containing both active and inactive organo-rhodium catalyst by binding active catalyst and impurities to an acidic ion exchange resin containing an acidic group. The purified hydroformylation stream can be returned to the hydroformylation reactor. All or a portion of inactive rhodium can be reactivated before recycling purified hydroformylation process stream to the reactor. During regeneration of the resin, a neutral solvent is used first to remove impurities which are discarded, then an acidic solvent is used to remove active organic rhodium catalyst from the resin. Such active catalyst can be rehydrided and returned to the hydroformylation reactor. An ion exchange resin having at least one acid group disposed on a silica backbone and an active organo-rhodium complex from a hydroformylation process stream bound to the resin can be produced.

18 Claims, 1 Drawing Sheet

HYDROFORMYLATION PROCESS WITH SEPARATION AND RECYCLE OF ACTIVE RHODIUM CATALYST

This Application claims the benefit of U.S. Provisional Application 60/001,212 filed on Jul. 18, 1995. This application is also continuation-in-part of application Ser. No. 08/673983, filed Jul. 1, 1996.

FIELD OF THE INVENTION

The invention relates to an improved hydroformylation process including purifying hydroformylation process streams by the separation of active rhodium catalyst from inactive rhodium catalyst and removal of impurities in hydroformylation process streams, recycling of active rhodium catalyst, removing impurities from recycle streams and recovery of rhodium metal catalysts. The separation of active from inactive catalyst enables recycling of active rhodium metal catalyst and removing all or a portion of inactive rhodium metal catalyst for regeneration and/or recovery of rhodium metal from inactive catalyst recycling.

BACKGROUND OF THE INVENTION

Rhodium metal compounds are commonly used as catalysts for organic reactions. One such process is hydroformylation. In the hydroformylation process, olefins are reacted with hydrogen and carbon monoxide to give linear (n-) and branched (iso-) aldehydes. The most common example is the manufacture of butyraldehyde from propylene and a hydrogen-carbon monoxide synthesis gas:

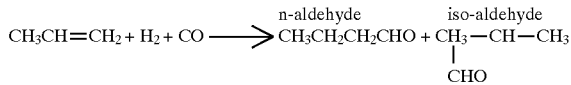

Linear aldehyde is a versatile chemical intermediate in the production of alcohols and plasticizers and is produced on a scale of about 4.4 million metric tons per year worldwide. Rhodium complex catalyst systems are typically utilized to permit the use of lower reaction temperatures which favor the production of these linear aldehydes.

Initially despite their high activity, simple rhodium compounds were not attractive because they gave mostly branched aldehydes, for example, isobutyraldehyde, from propylene. The addition of phosphorus ligands, however, such as triphenylphosphine or triphenylphosphite was found to give active catalysts with excellent selectivity for formation of the desired linear aldehydes. In the presence of this catalyst, propylene reacts with the synthesis gas to give predominantly n-butyraldehyde. The selectivity to the desired linear aldehyde is very high, greater than 90% when excess phosphorus ligand is present. The ligand is important to stabilize the catalyst during product recovery as well as to direct the reaction to formation of the desired product. Since both selectivity and stability are favored by a large excess of ligand, molten triphenylphosphine is an ideal solvent for the reaction, and the catalytic rhodium complex is stable almost indefinitely in this medium.

In a continuous catalytic hydroformylation process with molten triphenylphosphine (TPP) as the more volatile constituents are separated and, rhodium catalyst remains in the recirculating higher-boiling and triphenylphosphine solvent. The build up of impurities in the recirculating solvent and the gradual deactivation of a portion of the rhodium catalyst prevent the hydroformylation process from operating continuously for an infinite duration. Typical impurities are aryl phosphine oxide, alkyl phosphine oxide, mixed phosphines, mixed phosphine oxides, high molecular weight organic compounds, and trace metals. Gradually, rhodium catalyst becomes deactivated for reasons not well understood but probably associated with the reaction temperature and the presence of the impurities. Higher process temperature can be used to affect the presence of inactive catalyst, as higher temperature can cause olefin to be driven off during the conversion process resulting in a lower olefin yield. When its catalyst activity drops to an unacceptable level, to maintain throughput the reactor is shut down, cleaned, and restarted, which for normal operation occurs approximately every two years.

Although the catalyst containing residue can be recycled to the hydroformylation process, the amount of residue progressively increases while the catalyst activity progressively decreases. In order to compensate for the drop in catalytic activity and maintain the aldehyde throughput, it would be desirable to add additional active rhodium catalyst and remove inactive catalyst and impurities.

Due to the high cost and scarcity of rhodium metal, numerous prior art processes have been developed to recover and reactivate the rhodium catalyst so that it may be used again in the hydroformylation process. An example of such a process involves concentrating a hydroformylation reaction mixture by a wipe film evaporator and then air oxidizing. The rhodium catalyst is then reactivated by exposure to synthesis gas. Such conventional recovery and reactivation processes for this purpose, however, have proved rather unsatisfactory since the hydroformylation process must be discontinued and the reactor shut down in order to recover and reactivate the catalyst. Furthermore, even after such a process, the reactivated catalyst cannot be reactivated to 100% of its original activity.

One known process involves removal of a portion of the process stream as a bleed stream i.e. a relatively small stream in comparison to quantity of recirculating solvent and catalyst. For example the bleed stream might remove 1 to 2 percent of the reactor contents per day. The bleed stream goes to a storage vessel and then when the storage vessel is full it is reactivated by removing butyl diphenyl phosphine and oxidizing the reforming catalyst. This technique would remove only about 0.5 kg of rhodium per day from the reactor. This process is not used because efficient operating conditions are now known that minimize butyl diphenyl phosphine formation and the reactor can run for two years without the necessity for removing a bleed stream. However, after two years the reactor must be emptied and recharged.

Other prior art rhodium recovery processes have also been developed. These conventional approaches are generally directed toward removing Group IX and X transition metals (Co, Rh, Ir, Ni, Pt, Pd,) and include extraction with aqueous solutions, addition of precipitating agents or a combination of these techniques. Extraction of Group IX and X metals from organic mixtures using aqueous acetic acid is disclosed in European Patent No. 0 255 389. Using aqueous amine solutions is disclosed in U.S. Pat. No. 4,292,196. Use of aqueous alkaline cesium salt solution and crown ether is disclosed in U.S. Pat. No. 4,363,765. Aqueous solutions of ionic organophosphines for rhodium recovery is disclosed in U.S. Pat. No. 4,935,550. Another rhodium recovery method using amine/HCN mixtures is disclosed in J. Am. Oil Chemists Soc. 54 (1977) 276.

Precipitation of the Group IX and X metal compound, followed by either extraction or filtration of the precipitate is a second general approach. Examples include precipitation by peroxide treatment of an organic mixture containing the Group IX and X metal catalyst (U.S. Pat. No. 3,547,964), reductive treatment with hydrogen/catalyst or a hydride reducing agent (U.S. Pat. No. 4,560,539), precipitation of agglomerated rhodium from neutralized distillation residues (U.S. Pat. Nos. 3,998,622 and 4,135,911), oxidation under basic conditions (U.S. Pat. No. 4,396,551), treatment with an organic sulfur compound to form a precipitate (U.S. Pat. No. 4,413,118) and treatment with a carboxylic acid to precipitate an active catalyst (U.S. Pat. No. 4,950,629).

None of these known processes, however, can be utilized continuously with a hydroformylation process. Moreover, most of these prior art processes which treat hydroformylation waste streams, require extensive pretreatment in order to remove residual organic compounds prior to recovering rhodium.

Ion exchange methods have also been used to recover rhodium metals from aqueous solutions, as described in U.S. Pat. Nos. 2,945,743 and 3,567,368. Basic ion-exchange resins have been used to recover rhodium as described in U.S. Pat. No. 3,755,393. Group VIII metals have also been recovered from organic solutions using either a solid absorbent, such as calcium sulfate, molecular sieves, or an anionic ion-exchange resin as disclosed in U.S. Pat. No. 4,388,729.

Acidic ion exchange resins have also been used to recover Group IX and X transition metals. U.S. Pat. No. 5,114,473 discloses using a phosphorus containing ion-exchange resin which weakly binds the transition metal. U.S. Pat. No. 4,113,754 discloses using sulfonic acid resins which swell when contacted with different solvents and require pretreatment of the process streams which takes several days and precludes incorporating catalyst recovery into a continuous process. U.S. Pat. No. 5,208,194 discloses acidic ion-exchange resins containing sulfonic acid groups to bind a Group VIII transition metal carbonyl complex which is recovered by burning off (ashing) the resin.

The prior art processes using acidic ion-exchange resins to recover and reactivate Group IX and X transition metals such as rhodium metal from organic solutions are batch processes, i.e., not continuous.

SUMMARY OF THE INVENTION

The present invention provides an improved hydroformylation process having one or more of the following improvements: selectively separating active rhodium catalyst from inactive rhodium catalyst; removing active rhodium catalyst from a hydroformylation stream; removing impurities from a hydroformylation stream; recovering and reactivating inactive rhodium catalyst from a hydroformylation process stream; recycling reactivated catalyst; and rehydriding and recycling active catalyst previously removed from a hydroformylation process stream containing impurities.

Selective separation of active rhodium catalyst from inactive rhodium catalyst contained in a hydroformylation process stream containing both active and inactive organo-rhodium catalyst complex is accomplished with an ion exchange resin having a functional acid group attached to a silia-containing backbone.

A method for recovering an organo-rhodium catalyst from a hydroformylation process stream containing an organo-rhodium catalyst complex comprises the steps of (a) purifying a hydroformylation process stream containing triphenylphosphine, active organo-rhodium catalyst complex, inactive organo-rhodium catalyst complex and impurities with an ion-exchange resin containing an acidic group whereby active organo-rhodium catalyst complex and impurities in the process stream become bound to the resin; (b) separately removing impurities and active organo-rhodium catalyst complex from the resin; (c) rehydriding and recycling active rhodium catalyst removed from the resin; and (d) recycling purified hydroformylation process stream to the hydroformylation process.

The method can further include after step (a), the step of reactivating all or a portion of the deactive catalyst in the purified hydroformylation process stream and returning reactivated catalyst to a hydroformylation reactor.

The process is based on the discovery that contacting a hydroformylation stream containing active and inactivated organo-rhodium catalyst with certain acidic ion-exchange resins results in selective separation of active from inactive organo-rhodium catalyst due to active catalyst being more strongly bond to the resin as are certain impurities present in the stream.

Suitable resin include resin having an sulfonic acid group or carboxylic acid group which bind organo-rhodium catalyst in a portion of the hydroformylation stream. Examples of ion exchange resins having acidic group such as aromatic sulfonic acid, carboxylic acid, and propyl sulfonic acid are sold under the trademark Bakerbond by J. T. Baker Chemical Company, and cross-linked acidic 3-sulfopropyl methacrylate resins.

The resin with the bound active organo-rhodium catalyst complex and impurities is regenerated and active catalyst after being rehydrided is recycled to the hydroformylation process. Regeneration is a multi step process that separately removes active catalyst and impurities from the resin. Before regeneration, the resin is preferably washed with a solvent to remove any portion of the hydroformylation process stream (e.g. triphenylphosphine, aldehyde, reactor solvent, triphenylphosphine oxide, organic condensation product) and any unbound rhodium catalyst which can be recycled to the hydroformylation process. This solvent is selected so as not to interfere with the hydroformylation process when introduced into the hydroformylation reactor with recycled hydroformylation process stream. The resin is regenerated by first being washed with a solvent to remove a substantial portion of the impurities, e.g. aryl phosphine oxide, alkyl phosphine oxide, mixed phosphine oxide, and high molecular weight organic compounds. The resin after this first washing is substantially free of impurities and still binds the active organic-rhodium catalyst complex and a small portion of triphenylphosphine. The resin is then acidified by being washed with an acidified solvent to remove the bound active organo-rhodium catalyst complex. Acidification of the resin produces a rhodium-containing solution, from which the active rhodium catalyst is recovered and rehydrided so that it can be recycled to a hydroformylation reaction.

DETAILED DESCRIPTION OF THE INVENTION

Figure 1:
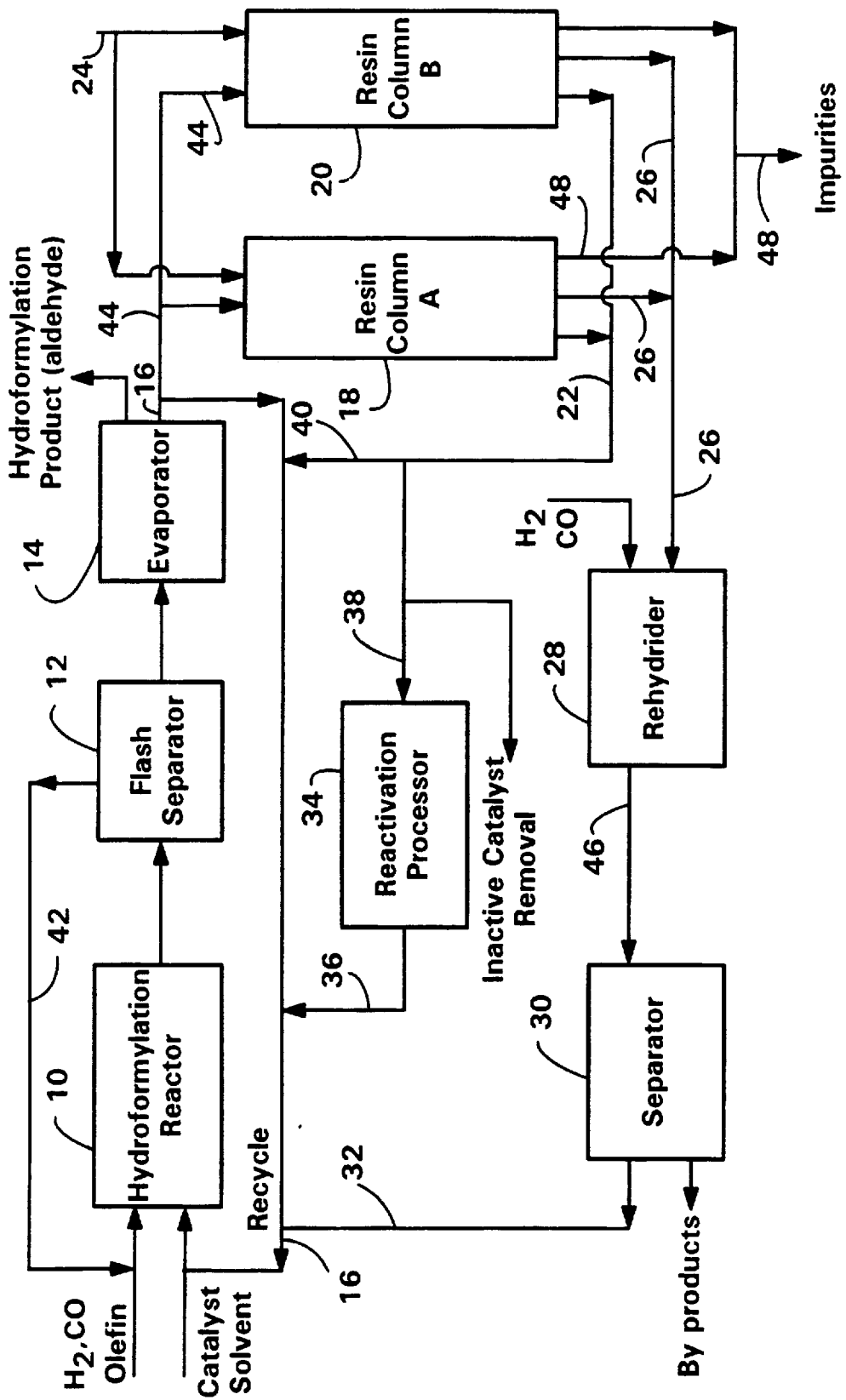
FIG. 1 is a process flow diagram for an improved hydroformylation process utilizing resin beds to separate active from inactive catalyst, purify a hydroformylation process stream, rehydrid active catalyst and reactivate inactive rhodium catalyst.

The process of the present invention provides a process for treating a hydroformylation process stream that: (a) removes impurities from the hydroformylation process stream; (b) selectively separates active rhodium from inactive catalyst in the hydroformylation process stream; (c) rehydrides and recycles active catalyst; (d) recycles a purified hydroformylation process stream; and, (e) reactivates inactive rhodium catalyst and recycles reactivated rhodium catalyst to the hydroformylation process. The process utilizes an acidic ion exchange resin for purifying the hydroformylation process stream and for selectively separating active from inactive rhodium catalyst contained in the stream. Removing of impurities and selective separation of active from inactive Rhodium catalyst from a hydroformylation process stream can be accomplished because of the selective binding characteristics of a particular type of acidic ion exchange resins. When a hydroformylation process stream containing impurities, active rhodium catalyst and inactive rhodium catalyst contacts the resin, impurities and active catalyst are bond to the resin. This simultaneously removes impurities such as mixed phosphines and phosphine oxides and active catalyst from a hydroformylation process stream containing triphenylphosphine, even in the presence of hydroformylation products (aldehydes), reactants and/or inactive rhodium catalysts. With such resins, recycling of active catalyst to a hydroformylation reactor and removal of impurities from the hydroformylation process can be continuously practiced with an appropriate sequence of process steps depicted in FIG. 1. The recovery method can be applied to any hydroformylation process stream that contains impurities from the hydroformylation reaction and/or active and inactive rhodium catalyst. Reaction product from the hydroformylation process, such as aldehydes may be present or can be removed before treating the process stream with the resin. Thus streams containing product and those streams having a high level of impurities can be treated to remove impurities and separate active from inactive rhodium catalyst.

A substantially improved hydroformylation process is shown in the FIG. 1 having better control of the level of catalytic activity and impurity concentrations in the hydroformylation reaction vessel. This is accomplished by using an acidic ion exchange resin for separating active from inactive rhodium catalyst and removing impurities from the hydroformylation stream containing triphenylphosphine and solvents. Typically the catalytic activity of a rhodium catalyst in a hydroformylation process will degrade at an increasing rate per day of operation of the process. Thus, in order to maintain a constant level of catalytic activity in a hydroformylation reactor, a sufficient quantity of active catalyst must be added to the reactor to compensate for the daily loss in catalytic activity. With the present invention the source of active catalyst can be recycled active rhodium catalyst, inactive catalyst that has been reactivated, fresh rhodium catalyst, or any combination thereof. Preferably, the purified hydroformylation stream is recycled continuously after passing through the acidic resin column. A portion of the purified hydroformylation process stream can be removed as a bleed stream as shown in FIG. 1 to further control the accumulation of undesirable chemicals due to recycling.

The purification and catalyst recovery process according to the present invention can be utilized in combination with conventional hydroformylation processes to obtain an improved hydroformylation process approaching steady state catalytic activity level and control of the concentration of impurities thus producing a more uniform hydroformylation product. This is accomplished by treating at least a portion of a hydroformylation process stream containing rhodium catalyst and triphenylphosphine in a column containing an acidic ion exchange resin to remove impurities and active rhodium catalyst and recycling the purified stream to the hydroformylation reaction vessel. The active rhodium and the impurities can be removed from the resin column, separated and the active catalyst can be returned to the hydroformylation process. Inactive catalyst in the purified stream can be reactivated prior to being recycled to the hydroformylation reaction vessel.

The impurities and catalyst can be separately removed from the resin and the resin regenerated by washing the resin to remove organic and phosphorus compounds and acid solvent washing the column to remove the active rhodium catalyst from the resin column, and preferably recycling the active catalyst to the hydroformylation process. The regenerated resin is also reused.

The term "hydroformylation process stream" as used herein is defined as any stream which is obtained from any point in a hydroformylation process and containing active and inactive rhodium catalyst and hydroformylation impurities. Examples of such catalysts are rhodium complexed with phosphorus ligands, typically comprising rhodium in solvents such as 2,2,4-trimethyl-1,3-pentanediol mono (2-methypropanoate) containing a substantial amount of phosphorous ligands such as triphenylphosphine or triphenylphosphite.

The top portion of FIG. 1 depicts a typical prior art hydroformylation process comprising a series of steps including hydroformylation in reactor 10, separation of unreacted ingredients such as $H_2$ CO and olefin from the hydroformylation process stream, in separator 12 followed by removal of aldehyde product in evaporator 14. Reactants feed into reactor 10 are hydrogen, carbon monoxide, and an olefin to be converted into an aldehyde by hydroformylation. The catalyst added to reactor 10 is a conventional organo-rhodium catalyst, i.e. complexed with phosphorus ligands, typically comprising rhodium in solvents such as 2,2,4-trimethyl-1,3-pentanediol mono (2-methypropanoate) and containing a substantial amount of phosphorous ligands such as triphenylphosphine or triphenylphosphite. The catalyst stream is introduced into the hydroformylation reactor 10 in order to provide catalyst for the reaction. On process start-up, the catalyst stream ordinarily comprises fresh catalyst and solvent. In a conventional process, after start-up, the catalyst in reactor 10 is composed of recycle stream 16 with fresh catalyst added as necessary to make up for degradation in catalyst activity in reactor 10 and catalyst losses. Unreacted low boiling point components remaining after hydroformylation are removed in flash separators 12. In conventional hydroformylation processes the light ends ($H_2$, CO and olefin such as propylene), shown as stream 42 in FIG. 1 are driven off in separator 12 and may be recycled. This is followed by an evaporation step as shown by evaporator 14 from which aldehyde product is removed. The residue or unvaporized portions from evaporator 14 is removed as recycle stream 16 which includes active and inactive catalyst, solvent, ligands, impurities, and sometimes a small quantity of product and unreacted feed chemicals. Stream 16 can be recycled back to reactor 10, with or without rhodium catalyst separation and impurity removal prior to recycling to reactor 10.

The continuous hydroformylation process of the present invention reduces the need to add fresh catalyst to the hydroformylation process for controlling catalytic activity. The improvement treats at least a portion of recycle stream 16 containing active and inactive rhodium catalyst, ligands and impurities to selectively separate active rhodium from inactive rhodium catalyst and to remove impurities from stream 16. Although all of stream 16 can be treated in a resin column, preferably a bleed stream 44 is removed from direct recycle stream 16, the latter returning untreated catalyst to the hydroformylation reactor in the same manner as a conventional recycle stream. Bleed stream 44 is treated within acidic ion exchange resin column 18 or 20 which selectively removes impurities and active rhodium catalyst from bleed stream 44. Impurities and active rhodium catalyst can be subsequentially separated from the resin during regeneration of the resin column (e.g. 18 or 20) by ion exchange. After removal of active rhodium catalyst during regeneration of the ion exchange resin the active catalyst needs to be rehydrided before being reintroduced into the hydroformylation reactor 10. This can be accomplished in reactor 28 where active catalyst stream 26 obtained during regeneration of the ion exchange resin is contacted with $H_2$+CO. The rehydrided active rhodium catalyst 46 is preferably separated from byproducts in separator 30 by processes such as filtration or a phase split which can remove unwanted by-products from rehydriding. The active rhodium catalyst-solvent stream 32 after being rehydrided is recycled to the hydroformylation reactor.

The process can be described in greater detail with reference to FIG. 1. Conventional hydroformylation is shown in the top portion of FIG. 1 which involves; hydroformylation of an olefin in reactor 10 usually at elevated temperature and pressure in a stream containing $H_2$, CO, olefin, conventional rhodium catalyst complex and trisphenylphosphine; separation of unreacted chemicals ($H_2$, CO and olefin) in separator 12; removal in 14 of hydroformylation products usually by evaporation; and, recycling of stream 16 containing reaction solvents, ligands and rhodium catalysts. The improvement provided by the present invention in a conventional hydroformylation process comprises (a) treating at least a portion of recycle stream 16 in a resin column, i.e. 18, to remove impurities and active rhodium catalyst to produce purified recycle stream 22; (b)returning at least a portion 40 of purified recycle stream 22 to the hydroformylation reactor 10; (c) sequentially removing impurities 48 and then removing active rhodium catalyst from resin column 18 with catalyst removal solvent 24 to produce stream 26 containing active rhodium catalyst for recycling; (d) treating active rhodium recycle stream 26 in rehydridor 28 with $H_2$ and CO to produce rehydrided active rhodium catalyst stream 46; (e)removing undesirable byproducts of rehydriding from stream 46 in separator 30; and (f) recycling active rehydrided rhodium catalyst 32 to the hydroformylation reaction in reactor 10. Optionally, inactive rhodium catalyst contained in purified recycle stream 22 can be reactivated according to conventional technology such as by wipe film evaporation, followed by oxidation and subsequent reduction by treating all or portion 38 of stream 22 in reactivation processor 34 to produce reactivated recycle stream 36. The level of catalytic activity in reactor 10 can be controlled by selecting the portion 38 of recycle stream 22 so that the quantity of reactivated catalyst in stream 36 approximately equals the amount of catalytic activity being lost in reactor 10.

When the hydroformulation reaction is being operated on a continuous basis, the rate that catalytic activity is being lost can be counterbalanced to maintain level catalytic activity by adjusting the proportion of stream 38 to stream 22 so that the rate that catalyst is being reactivated in 34 and returned to reactor 10 through recycle stream 36 approximately equals the rate that catalyst is being deactivated in reactor 10. Prior to the present invention separation of active from inactive catalyst was not achievable and both active and inactive catalyst had to be put through the reactivation step in order to recycle reactivated catalyst to reactor 10.

The catalytic activity of the improved hydroformylation process can be controlled by controlling the amount of active catalyst entering the hydroformylation reactor 10. The amount of active catalyst entering reactor 10 equals the sum of (1) active rehydrided rhodium catalyst in stream 32, (2) reactivated catalyst in stream 36 and fresh make up catalyst added to reactor 10. Catalytic activity can be maintained at a uniform level in reactor 10 by controlling the quantity of the catalyst reactivated in processor 34 and recycled in stream 36 to compensate for the amount of catalyst becoming deactivated in the hydroformylation process and by adding an amount of fresh catalyst to reactor 10 to make up for catalyst losses in the separation steps and resin regeneration. The quantity of catalyst reactivated in processor 34 can be controlled by sending only a portion of stream 22 to the reactivation processor 34 and directly recycling stream 40 without reactivation of the catalyst in stream 40.

Purification of hydroformylation process stream 16 and separating active from inactive catalyst can be practiced continuously by utilizing more than one resin column. FIG. 1 shown two resin columns, 18 and 20. Continuous operation can be achieved by regenerating one column, e.g. 18, while another column is treating stream 16. In this way a continuous or almost continuous source of purified recycle stream 22 is obtained from the column treating stream 16 while a continuous or almost continuous source of stream 26 containing active catalyst can be obtained from the other column being regenerated.

The key step of the process method comprises the step of contacting at least a portion of a hydroformylation process stream 16 containing triphenylphosphine, active rhodium catalyst, inactive rhodium catalyst and impurities with the acidic ion-exchange resin. The resin has a silica-containing backbone with a functional acid group attached to the silica. The acid group is typically selected from the group consisting of an aromatic sulfonic acid, an aliphatic sulfonic acid, an aromatic carboxylic acid, and an aliphatic carboxylic acid. The present invention also includes an intermediate composition having at least one sulfonic acid group disposed on a silica backbone and an organo-rhodium complex from a hydroformylation process stream bound to the resin.

Prior to using the acidic ion exchange resin for the first time the resin is preferably pretreated by washing with a variety of solvents in order to ensure that the active groups on the resin have an acidic structure rather than a salt structure, e.g. for a sulfonic acid resin, a sulfonic acid structure and not a sulfonate salt structure. This pretreatment comprises first washing the resin with an acidified solvent, followed by washing and adjusting the effluent pH to neutral. Before use the column may be washed with a resin pretreatment stream which comprises a suitable solvent such as dialcohol ester solvent, sold under the trade name TEXANOL by Eastman Chemical Company, which will not interfere with a hydroformylation process. This solvent is an ester alcohol having the chemical name 2,2,4-trimethyl-1, 3-pentanediol mono (2-methypropanoate). Another suitable solvent is 2,2,4-trimethyl-1,3-pentanediol monoisobutyrate. This final wash converts the solvent held upon the column to 2,2,4-trimethyl-1,3-pentanediol mono (2-methypropanoate), this will allow the solution from the column to be recycled back to the reactor. Without this step the introduction of another solvent to the reactor could occur which is preferably avoided.

Operation of the Column

After the resin is charged into the column active rhodium catalyst and impurities can be removed from stream 16 with the acidic ion exchange resin. Stream 16 contains an organo-rhodium catalyst complex and is passed through the column containing the resin in order to bind at least a portion of the active rhodium catalyst to the sulfonic or other active acid groups of the resin. Typically the active organo-rhodium catalyst is a complex with a Phosphorus Ligand such as TPP (triphenylphosphine). Stream 16 is passed through the resin column for a period of time up to the time for saturation the resin, e.g. about 100 g of process stream/g of resin. Once saturated the resin with bound active organo-rhodium catalyst complex can be regenerated.

Regeneration of Resin

The resin column to be regenerated is first isolated from the hydroformylation process by cutting off the flow of stream 16 to the resin column. A first solvent stream or pre-wash is added through line 24 to remove or displace remaining hydroformylation stream 16 containing unbound organo-rhodium catalyst complex from the column. Preferably the first solvent is compatible with the hydroformylation reaction and the pre-wash from the column is recycled back to reactor 10 with stream 16 containing unbound organo-rhodium catalyst complex. 2,2,4-trimethyl-1,3-pentanediol mono (2-methypropanoate) solvent is preferred as the first wash solvent because it is the solvent for adding catalyst to the hydroformylation reactor 10.

After the optional pre-wash, regeneration of the resin column is accomplished when the resin column is washed with a second solvent to remove from the resin, impurities originally contained in stream 16 such as aryl phosphine oxide, alkyl phosphine oxide, mixed phosphine oxide, and high molecular weight organic compounds. The heavy organic compounds are organic condensation products which otherwise build up in reactor 10. The preferred solvent for this purpose is alcohol. This washing off of impurities produces a resin having bound active organo-rhodium catalyst complex substantially free of impurities. The effluent from this impurities wash is removed as a waste stream 48 and disposed of. It should be noted that during this impurities wash the resin still holds (binds) the bound active organo-rhodium catalyst complex. This selective holding (binding) by the resin permits separation and removal of impurities. The impurities if not removed can accumulate and contribute to poisoning the catalyst (i.e., decrease the activity of the catalyst) and lead to extinction of the hydroformylation process over time.

After the wash with alcohol or other non acidic solvent to remove bound impurities from the resin, the resin is then acidified using an acidified solvent such as hydrochloric acid in isopropanol to remove the bound active organo-rhodium catalyst complex and produce a solution 26 containing active rhodium catalyst in the form of an organo-rhodium catalyst complex. Typically this would be $(TPP)nRH^{(I)}Cl$. This acidified solvent can comprise an alcohol (such as isopropyl alcohol and methanol), THF, toluene, or heptane in conjunction with an acid such as hydrochloric. If an acidified alcohol or heptane is used as the acidified solvent, the resin must also be washed using a fourth solvent such as toluene or tetrahydrofuran in order to prevent the organo-rhodium catalyst complex from precipitating onto the resin.

In acidifying the resin and removing active catalyst, the more acidic the solvent, the faster the active organo-rhodium complex catalyst is released from the resin. The acidic solvent used should have a pH below 4 with 1 to 4 being preferred to remove the organo-rhodium catalyst complex, although a solvent with a pH less than 1 may be used. This step serves two purposes it removes the active catalyst from the resin and it also reactivates (i.e. regenerates) the resin so that it will bond more active catalyst. Catalyst in stream 26 obtained during regeneration with the acidic solvent is active but it is in a form that is not compatible with the hydroformylation reactor 10. It is made compatible by rehydriding in reactor 28.

Rehydriding

The active organo-rhodium complex catalyst and solvent stream 26 obtained during regeneration of the acidic ion exchange resin is introduced into a rehydridor reactor 28 for rehydriding the organo-rhodium complex catalyst by reacting it $H_2$ and CO. Stream 26 consists of active catalyst, e.g. (Phosphorus Ligand)$_n$Rh(I)$^x$ complex in the acidic solvent, wherein X is Cl if HCl is used as the solvent. Active catalyst is obtained from the resin in the column with the acidified solvent. The most economical means for rehydriding is to place reactor 28 under pressure with of $H_2$ and CO. Triphenylphosphine (TPP) can be added to reactor 28. An acid scavenger such as Triethyl amine may also be added to scavenge the HCL. This reaction generates an active rhodium catalyst species. Rehydriding of active organo-rhodium catalyst complex can be also accomplished by contacting stream 26 with a hydriding agent such as sodium hydride, sodium borohydride, or aluminum trialkyl introduced into reactor 28. This will convert the (Phosphorus Ligand)$_n$Rh$^{(I)}$Cl to (Phosphorus Ligand)$_n$Rh$^{(I)}$H. The rehydrided catalyst is removed from reactor 28 as stream 46 and introduced into separator 30 where an amine hydrochloride and/or sodium chloride by-products are removed such as by filtering or by a phase split.

The stream 32 from separator 30 contains rehydrided organo-rhodium complex catalyst (preferably in a solution of 2,2,4-trimethyl-1,3-pentanediol mono (2-methypropanoate) and is recycled back into the hydroformylation reactor 10. The recycle process can be operated continuously in according to conventional chemical engineering practices in order to maintain a steady state activity level of the catalyst in the hydroformylation reaction. Typically, this is accomplished with multiple ion exchange columns with one being regenerated while one is separating catalysts and removing impurities from stream 16.

After removal of the active catalyst the resin can be washed with a solvent such as a neutral pH solution of 2,2,4-trimethyl-1,3-pentanediol mono (2-methypropanoate) solvent after regeneration before being placed back into service treating stream 16 in order to prepare for a new cycle of binding and removing active rhodium catalyst from a hydroformylation process output stream.

Several polar and non-polar solvents including: heptane, 2,2,4-trimethyl-1,3-pentanediol mono (2-methypropanoate), tetrahydrofuran (THF), methanol, and isopropyl alcohol and mixtures thereof can be used in the process as the solvent for a prewash of the ion exchange column before regeneration. The prewash solvent must be primarily non-polar and neutral pH so as not to remove impurities or active catalyst from the resin. However a prewash is not necessary in practicing the invention. During regeneration, the first wash to remove impurities must be primarily with a polar solvent at about neutral pH so as to remove impurities but retain most of the active catalyst on the resin. The removal of active catalyst from the resin is accomplished with acidified solvent, either polar or non-polar and at a pH of 4 or less. It has been observed that non-polar solvents release less Rh from the resin than polar solvents. When heptane is used as the pre-wash solvent less than 1.0% of the Rh is removed. When 2,2,4-trimethyl-1,3-pentanediol mono (2-methypropanoate) is used as the pre-wash solvent less than 4.5% of the Rh is removed. This effluent from a pre-wash can be returned to the reactor; therefore, there is no loss of Rh from reactor for this pre-wash step (this is especially true when using 2,2,4-trimethyl-1,3-pentanediol mono (2-methypropanoate) is used). The effluent 48 from resin wash with a polar solvent is diverted away from the reactor because stream 46 contains a bulk of the impurities such as TPPO and organic heavies that should be removed from the reactor. The use of tetrahydrofuran (THF) as the polar solvent wash can remove up to 2% of the Rh from the resin. The use of alcohols (such as methanol or isopropyl alcohol) as the polar solvent can remove as much as 46 of the Rh from the resin.

The preferred pre-wash solvent is 2,2,4-trimethyl-1,3-pentanediol mono (2-methypropanoate). Other possible pre-wash solvents include: alkanes (heptane, hexane(s), octane (s)), toluene, and xylene(s).

The preferred polar solvent is tetrahydrofuran (THF). Other possible wash solvents for removal of impurities include, alcohols (methanol, isopropyl alcohol, butanol(s), 2-ethyl-1-hexanol), ethers (methyltert-butyl ether, butyl ether), ketones (acetone, methyl ethyl ketone, methyl propyl ketone), toluene, and xylene(s).

Operation with Two Columns

Preferably, the present invention is operated with more than one column. After the acidic ion exchange resin in column letter A or B, has absorbed impurities and active rhodium catalyst it can be regenerated while another column is used to treat stream 16 sequentially. During regeneration impurities as stream 48 are removed which are discarded from the hydroformylation process. Then active rhodium catalyst is removed from the resin in stream 22 and recycled back to the hydroformylation reactor 10 after being rehydrided. The following steps are the preferred regeneration process of column A while column B is treating stream 16: (1) wash the resin in column A with a non-polar pre-wash solvent, such as 2,2,4-trimethyl-1,3-pentanediol mono (2-methypropanoate). This wash will remove the non-bonded Rh, and a small percentage of the TPP, TPPO, and organic heavies from the column and return it to the reactor along with stream 16;

(2) A first wash solvent preferably tetrahydrofuran (THF) is passed through column A to remove the bulk of impurities such as the TPP, TPPO, and organic heavies as stream 48. Stream 48 is discarded from the hydroformylation process. (In preferred case the THF and 2,2,4-trimethyl-1,3-pentanediol mono (2-methypropanoate) can be distilled over head from stream 46 and reused);

(3) The active Rh catalyst is removed from the column as stream 26 with an acidified solvent.

The preferred acidified solvent is a blend of THF and isopropyl alcohol that has been acidified with an acid such as hydrochloric acid to a pH below 4. Other possible wash solvents that can be acidified and used as the acidified solvent are: ketones (acetone, methyl ethyl ketone, methyl propyl ketone), ethers (methyl-tert-butyl ether, butyl ether), toluene, and xylene. The preferred acid is hydrochloric acid, other possible acids include hydrobromic, hydroiodic, formic, acetic, chloroacetic, fluoroacetic, dichloroacetic, trifluoroacetic, and trichloroacetic acids. Other acids such as citric, 2-ethyl-1-hexanoic, methyl sulfonic acids are believed to be effective.

Although stream 16 is shown in FIG. 1 as being separated from the reactor output after evaporator 14, alternatively it may be taken before the evaporator. In either case, stream 16 contains active and inactive rhodium catalysts and impurities such as aryl phosphine oxide, alkyl phosphine oxide, mixed phosphines, mixed phosphine oxide, and high molecular weight organic compounds which can be selectively removed with the acidic ion exchange resin.

The rhodium recovery process shown schematically in FIG. 1 comprises two resin columns A and B which are alternately contacted with stream 16. While one column is sorbing the active rhodium catalyst and impurities from stream 16, the separation of impurities from active rhodium catalyst by the regeneration steps disclosed above can be performed on the other column which has already been in contact with stream 16. Use of multiple columns increases the speed with which the continuous recovery process can be operated so that increased recovery speeds can be accomplished.

The resins used as the acidic ion exchange resin it must be capable of selectively binding active rhodium catalyst tightly enough to permit the removal of impurities from the resin during regeneration without removing active catalyst from the resin when washed with the neutral solvent and release the active rhodium catalyst when washed with the solvent with a pH of 4.0 or less. Moreover, the resin should not absorb inactive rhodium catalyst from stream 16 as readily as it absorbs active catalyst. Moreover, these resins preferably do not appreciably change volume (i.e., swell) when using the various solvents required by the recovery process, thus enabling continuous recovery within a resin bed, utilizing various polar & non-polar, protic and non-protic solvents without any special pretreatment or processing steps. These properties facilitate recycle of the resin and the catalyst in a continuous manner. Three selective separations are achievable with the acidic ion exchange resin. First, active rhodium and impurities are preferentially removed from hydroformylation stream 16 while in comparison to inactive rhodium catalyst which tend to remain in stream 16. Second, during regeneration of the resin, impurities can be selectively separated from active rhodium resin by appropriate selection of solvents used in regeneration of the resin. Impurities are preferentially removed from the resin with polar solvents that are essentially neutral e.g. a pH between 6 and 8 while active rhodium catalyst is retained on the resin. Third, active rhodium catalyst is removed from the resin with a solvent having a pH below 4.

Certain commercial resins were found to be effective. In general, the resins used in the present invention have a molecular structure in which an active group is attached to a cross-linked polymer or network polymer. The resins found effective (i.e., able to recover and reactivate a high proportion of the rhodium in the recycle stream) were an aromatic sulfonic acid, propyl sulfonic acid and carboxylic acid sold by J. T. Baker, under the name Bakerbond. All of the resins that contain sulfonate or carboxylate groups and a silica backbone are effective in binding the rhodium catalyst and did not swell while performing the continuous recovery process of the present invention. Also an acidic cross-linked 3-sulfopropyl methacrylate sulfonic acid resin is effective at selectively binding and sequentially releasing impurities and then active rhodium.

The commercially available aromatic resins suitable for use in the present invention can be manufactured by the condensation reaction of a hydroxy aromatic sulfonic acid and silica to produce the defined supported aromatic sulfonic acid resin on silica structure. A typical manufacturing method can comprise the condensation reaction of silica having a defined porosity, preferably with an average pore size of approximately 40 micrometers, with a hydroxy aromatic sulfonic acid to produce a supported aromatic sulfonic acid resin on silica with water as a by-product. This condensation reaction can be accomplished by adding the hydroxy aromatic sulfonic acid to the silica and heating it under vacuum at a temperature and for a time until the reaction is complete, i.e., until water is no longer is produced.

Aliphatic sulfonic acid resins and carboxylic resins useful in the present invention and discussed above can be manufactured in similar fashion by replacing the aromatic sulfonic acid starting material in the condensation reaction with either hydroxy aliphatic sulfonic acids or hydroxy aliphatic carboxylic acids respectively.

It is believed that the condensation reaction which occurs is between the hydroxyl group of the hydroxy acid and the hydroxyl group on the silica to produce a supported resin having an acidic group connected by a tether. The tethered acidic group acts as the active group for binding the rhodium. Depending on the starting material reacted with the silica, the tether is either an aromatic group or an aliphatic group and the acidic group is either a carboxylic acid or sulfonic acid. In the case of a sulfonic acid active group, the structure of the acid group which binds the rhodium is a sulfonate, $SO_3$—, group. In the case of a carboxylic acid active group, the structure of the acid group which binds the rhodium is a carboxylate, $CO_2$—, group.

Empirical rhodium recovery tests using the procedure set forth below were performed using these ion exchange resins to evaluate their efficacy in recovering rhodium catalysts from hydroformylation waste streams.

RESIN SELECTION

Following is a step-by-step process used to screen acceptable resins for Rh recovery. The structured procedure is similar to the Rh recovery test method, where the process parameters are first defined then the actual process steps are described.

Parameters

1) Test is performed at room temperature (20°–25° C.);
2) Flow rate, set pump to 1 mL/minute;
3) Active Rh must be isolated from a hydroformylation process stream;
4) The column containing the resin (material that will recover the Rh) has a diameter of 1 cm;
5) The quantity of resin used is 4.0 grams;
6) The balance of the column was filled with sand;
7) Treat process stream that contains 1 to 1.5 column volumes of process stream (4 to 6 grams of process stream). The trials performed using a phosphorus ligand, e.g., a TPP based hydroformylation process stream contained 1 to 1.5 milligrams of Rh charged to the resin, while the trials performed using a different ligand based commercial hydroformylation process stream contained 1.7 to 3.6 milligrams of Rh charged to the resin; and
8) The effluent from the column is isolated in three different fractions.

Column Preparation

1) Charged resin as a slurry in water;
2) Activated resin by passing 10 grams of 5 wt % HCl(aq) in methanol;
3) Pumped 10 grams degassed methanol across the column to remove impurities and to return the column effluent to a neutral pH (pH·6);
4) Pumped 10 grams degassed heptane across column;
5) Pump hydroformylation stream across column (4 to 6 grams at 250 to 600 ppm Rh), collect the effluent in the process stream collection flask;
6) Wash resin with 10 grams of degassed heptane, followed by a wash into 10 grams of degassed methanol, collect the wash effluent in the solvent wash collection flask;
7) Remove Rh from the column with 10 grams of 5 wt % $HCl_{(aq)}$ in methanol (pH<0), followed by 10 grams of methanol;
8) A second trial may be performed by returning to step three and repeating steps three through seven with a second fraction of hydroformylation process stream; and
9) Analyze the three collected fractions (process stream, solvent wash, and recovered Rh) for the Rh content, using ICP emission spectroscopy.

The experiments used a 1.5:1 or approximately a one to one ratio of grams of process stream to grams of ion exchange resin in the column. The elution flow rates (1 mL/min) and other conditions (e.g., room temperature) were kept constant unless otherwise noted. The following table lists the quantity of rhodium recovered using the different resins:

TABLE I

| RESIN TYPE % Rh RECOVERED | CONDITIONS | RESIN BACKBONE | ACTIVE GROUP |
|---|---|---|---|
| Aromatic* >95% | normal | silica gel | aromatic sulfonic acid |
| Propyl* 86.6% | normal | silica gel | propyl sulfonic acid |
| Propyl* 98% | Faster elution rates | silica gel | propyl sulfonic acid |
| CROSS-LINKED 3-sulfopropyl 1.6% methacrylate (salt) | normal | methyl and propyl methacrylate/TMPTMA | propyl sulfonate potassium salt |
| CROSS-LINKED 3-sulfopropyl 35.6% methacrylate (acid) | normal | methyl and propyl methacrylate/TMPTMA | propyl sulfonic acid |
| AMBERLYST** 7.0% X1010 | normal | styrene/divinyl benzene | sulfonic acid |
| AMBERLYST 13.8% | normal | styrene/divinyl benzene | sulfonic acid |
| AMBERLITE** 1% IRP-169 | normal | methacrylic acid/divinyl benzene | sulfonic acid |
| AMBERLITE 1% IRC-718 | normal | styrene/divinyl benzene | iminodiacetic acid |

*Sold by J. T. Baker under BAKERBOND brand name
**AMBERLYST and AMBERLITE are brand names of the Rohm and Haas Co.

Using the procedure outlined above the Bakerbond aromatic sulfonic acid resin recovered >95% of the active Rh. Amberlyst X1010 resin recovered 13.8% of the active Rh and Amberlyst 15 recovered 7.0% of the Rh.

As can be seen above, the sulfonic acid containing resins were found to be the most effective in binding active rhodium catalyst. Of these sulfonic acid containing resins, the aromatic sulfonic acid resin having a silica gel resin backbone gave superior results for preferentially absorbing active rhodium catalyst and impurities from hydroformylation process streams. It is believed that electronic and steric interactions between the resin and the catalyst affect the binding efficiency of the rhodium species to the active group of the resin. Thus resin backbones, e.g., silica gel backbone may have an effect upon the quantity of rhodium recovered.

It was also discovered that the propyl sulfonic acid containing resin, although the most effective in binding rhodium, was not as effective in ultimately recovering the rhodium catalyst since a portion of the rhodium was not released during an acidic solvent wash at a pH below 4 and thus permanently bound to the resin.

Additionally, the acidic cross-linked 3-sulfopropyl methacrylate shown in Table 1 above was developed as a resin useful in a continuous recovery process. It was not as effective, as the other resins tested. Thus, the binding properties of the above resins permit rhodium containing catalysts to be selectively bound and then released so that the catalyst can be recovered and the resin reused continuously.

While the resins disclosed above are useful in the continuous rhodium recovery process of the present invention, it will be appreciated that other resins may be utilized in conjunction with the method as taught above. The resins, to be useful in the process, must meet the criteria that they selectively bind active rhodium catalyst tightly enough to permit the removal of impurities from a hydroformylation process stream containing active and inactive rhodium catalyst and impurities yet loosely enough to permit sequential removal of impurities and then active rhodium resin removal if the catalyst from the resin when desired.

The four resin listed above, are all acidic ion exchange resins. The Amberlite resins do not appear to recover rhodium while the amberlyst resins recover a limited quantity of rhodium. The Bakerbond products recovered >95% of the rhodium.

After using the initial screening test, the following test method is used to indicate the ability of the resin to perform in a commercial process.

The process parameters are first defined then the actual process steps are described. Any resin (material) that recovers greater or equal to 15% of the charged active rhodium using the following step-by-step process can be used in the process of the invention.

Parameters
1. Test is performed at room temperature (20°–25° C.)
2. Flow rate, set pump to 2 mL/minute
3. Rh must be isolated from a hydroformylation process stream
4. The column containing the resin (material that will recover the Rh) has a diameter of 1 cm
5. The quantity of resin used is 4.0 grams
6. The balance of the column should be filed with an inert packing material such as sand or silica
7. Treat process stream that contains 5 milligrams of Rh (20 grams of process stream containing a concentration of 250 ppm of Rh)
8. If process stream contains more than 250 ppm of Rh dilute with butanal to achieve 250 ppm Rh, if process stream contains less than 250 ppm Rh strip aldehyde in stream to achieve 250 ppm Rh
9. The effluent from the column is isolated in three different fractions Column Preparation
1. Charge resin as a slurry in a suitable solvent (such as water or isopropyl alcohol)
2. Activate resin by standard procedure as recommended by the resin manufacturer
3. Pump 20 grams degassed isopropyl alcohol across the column to remove impurities and to return the column effluent to a neutral pH (pH>6)
4. Pump 20 grams degassed heptane across column
5. Pump hydroformylation stream column (20 grams at 250 ppm Rh), collect the effluent in the process stream collection flask
6. Wash resin with 10 grams of degassed heptane, followed by a wash with 10 grams of degassed tetrahydrofuran, collect the wash effluent in the solvent wash collection flask
7. Remove Rh from the column with 20 grams of 5 wt % $HCl_{(aq)}$ in isopropyl alcohol (pH<0), followed by 10 grams of tetrahydrofuran and 20 grams of 5 wt % $HCl_{(aq)}$ in isopropyl alcohol, collect in recovered Rh collection flask
8. A second trial may be performed by returning to step three and repeating steps three through seven with a second fraction of hydroformylation process stream
9. Analyze the three collection fractions (process stream, solvent wash, and recovered Rh) for the Rh content, using standard analytical methods (ICP is recommended)

Table II sets forth the test results showing the quantity of rhodium recovered using the above method.

TABLE II

| RESIN TYPE % Rh RECOVERED | CONDITIONS | RESIN BACKBONE | ACTIVE GROUP | |
| --- | --- | --- | --- | --- |
| Amberlyst X1010 | normal | styrene/divinyl benzene | sulfonic acid | 2.9% |
| J T Baker Diamino | normal | silica gel | diamino group | 1.1% |
| J T Baker Propyl sulfonic acid | normal | silica gel | sulfonic acid | 35.1% |
| J T Baker Carboxylic Acid | normal | silica gel | carboxylic acid | 38% |
| J T Baker Aromatic Sulfonic Acid | normal | silica gel | Aromatic sulfonic acid | 39.9% |

Criteria for Selection of Resin
1. The quantity of active organo-rhodium catalyst recovered from the resin must be at least 15% of the active organo-rhodium catalyst charged to the column It should be noted that for the above processes, while other process parameters did influence rhodium recovery, these parameters had less of an effect on the recovery process than the type of resin used. The elution rate is important. Therefore, slow flow rates of the solvents (e.g. 2–5 mL/min for a resin contained in 1×10 cm column) are better than fast flow rates because the adsorption of Rh is not instantaneous.

Alternate Rehydriding Methods
An alternative method for rehydriding the active rhodium in small reactor 28 is to pressurize reactor 28 with hydrogen gas and/or synthesis gas ($H_2$ and CO) in the presence of an acid scavenger such as methyl or ethyl amines, pyrridine, hydrazine, etc., prior to filtering off the acid-base adduct or by-product stream in separator 30. This also will convert the (Phosphorous Ligand)nRh(I)Cl to (Phosphorous Ligand)nRh(I)H and capture the HCl acid with the acid scavenger as a byproduct. This is accomplished as follows:

1) The active Rh catalyst is removed from the resin as the (Phosphorous Ligand)$_n$RhCl complex in a polar solvent such as alcohols (methanol, isopropyl alcohol), THF, toluene, xylene, acetone and methyl ethyl ketone at a pH below 4.

2) An acid scavenger is added to the reactor 28 such as an amine (triethylamine, diethylamine, tripropylamine, dipropylamine) pyridine and hydrazine.

3) Add Phosphorous Ligand (e.g., TPP) to the reactor 28. The preferred quantity of TPP is 10 to 30 moles of TPP per mole of Rh, although the 5 to 200 moles of TPP per mole of Rh is acceptable.

4) Pressurize reactor 28 e.g. to 200 psig with $H_2$ and CO preferably at the same ratio as used in the hydroformylation process.

5) This will produce hydrided active rhodium catalyst, e.g. (Phosphorous Ligand)$_n$RhH and Hcl with the HCl scavenged by the base. This is stream 46 in FIG. 1.

6) Stream 46 in FIG. 1 filtered to remove the acid-base adduct produced by the scavenging of Hcl and produce stream 32.

7) Add 2,2,4-trimethyl-1,3-pentanediol mono (2-methypropanoate) to the filtered solution and recycle stream 32.

B. Rehydriding of Stream with Sodium Borohydride in an Alcohol

Stream 26 containing active organo-rhodium catalyst complex and solvent is introduced into reactor 28. Stream 26 consists of primarily of acidified active catalyst such as (Phosphorous Ligand)$_n$RhCl and non-coordinated Phosphorous Ligand in the acidic solvent. Rehydriding can be accomplished by contacting stream 26 in reactor 28 with a sodium borohydride and ethanol mixture. This will neutralize acid and rehydride the catalyst producing sodium chloride. The rehydrided rhodium catalyst can be precipitated, washed to remove impurities, suspended in 2,2,4-trimethyl-1,3-pentanediol mono (2-methypropanoate) and returned to reactor 10.

C. Rehydriding with Hydrazine in an Alcohol

Active organo-rhodium catalyst complex and acidic solvent are removed during regeneration as stream 26 and introduced into reactor 28. Stream 26 consists of acidified active rhodium catalyst e.g. (TPP)$_n$RhX, X is the counter anion of the acid that was used to release the organo-rhodium catalyst from the resin, and non-coordinated TPP in the acidic solvent. Rehydriding can be accomplished by contacting stream 26 with excess hydrazine charged as a solution of 95 hydrazine in water, in reactor 28. This will neutralize the acid in the solution producing hydrazine hydrochloride, while converting the (TPP)$_n$RhCl to the active (TPP)$_n$RhH. The by-product can be separated from the solution by filtering, the reactivated rhodium can be precipitated, washed to remove impurities, suspended in 2,2,4-trimethyl-1,3-pentanediol mono (2-methypropanoate) and recycled to the reactor 10.

D. Rehydriding with Hydrazine and Hydrogen Gas in Mixed Solvent

Rehydriding of stream 26 can be accomplished by adding an aromatic solvent to Stream 26 and contacting it with hydrazine and hydrogen gas, in reactor 28. This will neutralize the acid in the solution, e.g. if Hcl, it produces hydrazine hydrochloride, while converting the (TPP)$_n$RhCl to the active (TPP)$_n$RhH. The by-product can be removed from the solution by filtering, and the rehydriding rhodium catalyst can be precipitated, washed to remove impurities, suspended in 2,2,4-trimethyl-1,3-pentanediol mono (2-methypropanoate) and returned to reactor 10.

E. Rehydriding with Sodium Alkoxide in Alcohol

Stream 26 is introduced into reactor 28. Rehydriding can be accomplished by contacting stream 26 with sodium alkoxides, introduced into reactor 28 as sodium alkoxides in alcohols. This will neutralize the acid in the solution producing sodium chloride and alcohol, while hydriding the catalyst. For example, with Hcl as the acid the (TPP)$_n$RhCl is hydrided to the active (TPP)$_n$RhH. The sodium chloride can be removed from the solution by filtering the rehydrided rhodium can be precipitated, washed to remove impurities, suspended in 2,2,4-trimethyl-1,3-pentanediol mono (2-methypropanoate) and returned to the reactor.

What is claimed:

1. A method for purifying and separating active rhodium catalyst from inactive rhodium catalyst contained in a hydroformylation process stream comprising:

contacting at least a portion of said process stream with an acidic ion-exchange resin to bind impurities and active rhodium catalyst complex to said resin and produce a purified hydroformylation process stream containing inactive rhodium catalyst.

2. The method of claim 1, wherein said acid ion-exchange resin has a silica-containing backbone with a functional acid group attached to the silica.

3. The method of claim 1, wherein said ion-exchange resin has a functional acid group selected from the group consisting of an aromatic sulfonic acid, an aliphatic sulfonic acid, an aromatic carboxylic acid, and an aliphatic carboxylic acid.

4. A composition comprising an acidic ion-exchange resin having at least one acidic group disposed on a silica backbone and an active rhodium complex from a hydroformylation process stream bound to said resin.

5. The composition of claim 4, wherein said acidic group is selected from the group consisting of an aromatic sulfonic acid, an aliphatic sulfonic acid, an aromatic carboxylic acid, and an aliphatic carboxylic acid.

6. An improved hydroformylation process comprising a hydroformylation reaction of an olefin with $H_2$ CO in the presence of an organo rhodium catalyst complex to produce a hydroformylation process stream containing an aldehyde product, impurities, active organo rhodium catalyst complex and inactive organo rhodium catalyst complex, wherein the improvement comprises:

(a) passing at least a portion of said hydroformylation process stream through an acidic ion-exchange resin column to cause active rhodium catalyst complex and impurities to be bound to said resin and removed from the hydroformylation process stream to produce a purified hydroformylation process stream containing inactive organo rhodium catalyst complex;

(b) recycling the purified hydroformylation process stream to the hydroformylation reaction;

(c) removing the impurities from the resin column;

(d) removing the active organo rhodium catalyst complex from said resin column;

(e) rehydriding the active organo rhodium catalyst removed from the resin column; and (f) recycling the rehydrided active catalyst to the hydroformylation reaction;

wherein steps (c) and (d) result in regeneration of resin so that it is suitable for reuse in step (a).

7. The improved process of claim 6, further comprising after step (a), the step of:

washing the resin column with a solvent which can be introduced into the hydroformylation process without affecting said process to remove residual hydroformylation process stream and unbound rhodium catalyst.

8. The improved process of claim 6 wherein step (c) is performed by:
washing said resin with a solvent at a pH between 6 and 8 to remove impurities from the resin and resulting in said resin retaining active organo rhodium catalyst complex.

9. The improved hydroformylation process of claim 6, wherein:
said step (a) is accomplished by contacting a portion of the hydroformylation process stream with the acidic ion-exchange resin to cause said resin to bind at least fifteen percent (15%) of the active organo rhodium catalyst complex in said portion of said process stream;
said step (b) is accomplished by washing said resin with a solvent at a pH between 6 and 8 and results in the removal as impurities aryl phosphine oxide, alkyl phosphine oxide, mixed phosphine oxide, and high molecular weight organic compounds and results in a resin containing essentially bound active organo rhodium catalyst complex.

10. The process of claim 6, wherein said acidic ion exchange resin is disposed in at least two separate columns and step (a) is performed in the first of said beds while the second of said resin columns is being regenerated by the performance of steps (c) and (d).

11. The process of claim 1 wherein the acidic ion-exchange resin is a resin having a sulfonic acid group disposed on a silica backbone.

12. The process of claim 6 wherein after said organo rhodium catalyst complex is removed from said resin by washing with an acidic solvent, the catalyst is rehydrided with a hydriding agent to convert the organo-rhodium catalyst from $(L)_n Rh_{(I)} X$ to $(L)_n Rh^{(I)} H$, wherein L represents a phosphorous ligand.

13. The process of claim 12 wherein said hydriding agent is selected from the group consisting of sodium hydride, sodium borohydride and lithium aluminum hydride.

14. The process of claim 6 wherein said organo rhodium catalyst complex is $(TPP)_n Rh^{(1)} X$ and is removed from said resin by washing with an acidic solvent and rehydriding with hydrogen and triphenylphosphine to produce $(TPP)_n Rh^{(I)} H$ in the presence of an acid scavenger selected from the group consisting of $Me_3N$, pyridine, hydrazine, and $Et_3N$ to capture HCl.

15. The process of claim 6 wherein the removal of the impurities from the resin is with a solvent selected from the group consisting of isopropyl alcohol, tetrahydrafuran, ethanol, methanol, heptane.

16. The process of claim 6 wherein acidified solvent for removing said active catalyst from the resin is selected from the group consisting of isopropyl alcohol, methanol, and heptane in combination with an acid selected from the group consisting of hydrochloric, sulfuric and hydrobromic acid.

17. The process of claim 6 where in a portion of the purified hydroformylation process stream is removed from the process and replaced with fresh active rhodium catalyst and triphenylphosphine that are added to the hydroformylation reactor.

18. The process of claim 6 further comprising reactivating the inactive organo rhodium catalyst complex contained in at least a portion of the purified hydroformylation process stream and recycling the reactivated catalyst to the hydroformylation reaction.

* * * * *